(12) United States Patent
Grassy et al.

(10) Patent No.: US 7,024,311 B1
(45) Date of Patent: Apr. 4, 2006

(54) COMPUTER-AIDED METHOD FOR THE PROVISION, IDENTIFICATION AND DESCRIPTION OF MOLECULES CAPABLE OF EXHIBITING A DESIRED BEHAVIOR, MORE PARTICULARLY IN THE PHARMACEUTICAL SECTOR, AND MOLECULES OBTAINED BY SAID METHOD

(75) Inventors: Gérard Grassy, Perols (FR); Michel Kaczorek, Nimes (FR); Roger Lahana, Nimes (FR); Abdelaziz Yasri, Nimes (FR)

(73) Assignee: Synt:EM S.A., Nimes (FR)

( * ) Notice: Subject to any disclaimer, the term of this patent is extended or adjusted under 35 U.S.C. 154(b) by 0 days.

(21) Appl. No.: 09/359,181

(22) Filed: Jul. 22, 1999

Related U.S. Application Data

(63) Continuation-in-part of application No. PCT/FR98/02909, filed on Dec. 29, 1998.

(30) Foreign Application Priority Data

Dec. 30, 1997 (FR) ............................................ 97 16706

(51) Int. Cl.
  *G01N 33/48* (2006.01)
  *G01N 31/00* (2006.01)
  *G01N 33/53* (2006.01)
  *C12Q 1/68* (2006.01)

(52) U.S. Cl. ............................. 702/19; 702/22; 702/23; 702/127; 702/150; 702/155; 435/6; 435/7.1

(58) Field of Classification Search .................. 702/19, 702/22, 23, 127, 150, 155; 435/6, 7.1
  See application file for complete search history.

(56) References Cited

U.S. PATENT DOCUMENTS

| | | | | |
|---|---|---|---|---|
| 5,463,564 A | * | 10/1995 | Agrafiotis et al. | |
| 5,784,294 A | * | 7/1998 | Platt et al. | ..................... 702/27 |
| 6,182,016 B1 | * | 1/2001 | Liang et al. | |
| 6,185,506 B1 | * | 2/2001 | Cramer et al. | |
| 6,240,374 B1 | * | 5/2001 | Cramer et al. | |

FOREIGN PATENT DOCUMENTS

| | | |
|---|---|---|
| WO | WO 97/27559 | 7/1997 |
| WO | 98/46633 | 10/1998 |

OTHER PUBLICATIONS

Krieger (Chemical and Engineering News, (Feb. 12, 1996) vol. 74, No. 7, pp. 67–73).*
Krieger (Chemical and Engineering News,(Sep. 16, 1996) vol. 74, No. 38, pp. 30–37).*
Hruby et al. Biochem Journal (1990) vol. 268 pp. 249–262.*
Ajay et al. J Med. Chem. 1999, vol. 42 pp. 4942–4951.*
Grassy, Gerard., et al., "Computer–assisted rational design of immunosuppressive compounds." Nature Biotechnology 16 748–752 Aug. 1998.
G. Grassy, J. Fagart, B. Calas, M. Adenot, ME Rafestin–Oblin, G. Auzou, *Structure–activity relationships of steroids with mineralocorticoid activity*, Eur. J. Med. Chem. (1997), 32, 869–879.
A. Yasri, L. Chiche, J. Haiech and G. Grassy, *Rational Choice of Molecular Dynamics Simulation Parameters Through the Use of the Three–Dimensional Autocorrelation Method: Application to Calmodulin Flexibility Study*, Protein Engineering, vol. 9, No. 11, pp. 959–976 (1996).
Grassy et al., *Statistical Analysis and Shape Recognition: Applications to MD Simulations, conformational analysis and Structure–Activity Relationships*, Trends QSAR Mol. Modell, Proc. Eur. Symp. Struct.–Act. Relat., 1992, pp. 216–219.

* cited by examiner

*Primary Examiner*—Marjorie Moran
*Assistant Examiner*—Lori A. Clow
(74) *Attorney, Agent, or Firm*—Donald R. Piper, Jr.; Dann, Dorfman, Herrell & Skillman, P.C.

(57) ABSTRACT

The present invention is concerned with a computer-aided method for the provision, identification and description of molecules exhibiting a desired behaviour, more particularly in the pharmaceutical sector, employing a molecular modelling step, a combinatorial library building step and a step of selecting potentially useful molecules, said method including a step whereby the candidate molecules are filtered using a dynamic filter representing constraints of conformational variations which the molecules must satisfy in order to exhibit said activity.

7 Claims, No Drawings

```
                     SEQUENCE LISTING

<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 1

Arg Glu Asn Leu Arg Ile Ala Leu Arg Tyr
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 2

Tyr Arg Leu Ala Ile Arg Leu Asn Glu Arg
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 3

Arg Val Asn Leu Arg Ile Ala Leu Arg Tyr
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 4

Tyr Arg Leu Ala Ile Arg Leu Asn Val Arg
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 5

Asn Leu Arg Ile Ala Leu Arg Tyr Tyr Trp
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 6

Arg Val Asn Leu Arg Thr Ala Leu Arg Tyr
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 7

Arg Val Asp Leu Arg Thr Leu Leu Arg Tyr
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 8

Arg Val Asp Lys Arg Thr Leu Leu Gly Tyr
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 9
```

Arg Val Ser Leu Arg Asn Leu Leu Gly Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 10

Arg Glu Ser Leu Arg Leu Leu Arg Gly Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 11

Arg Glu Asp Leu Arg Thr Leu Leu Arg Tyr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 12

Glu Asn Leu Arg Ile Ala Leu Arg
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 13

Arg Glu Asn Leu Pro Ile Ala Leu Arg Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 14

Arg Val Asn Leu Arg Thr Leu Arg Arg Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic

```
-continued
<400> SEQUENCE: 15

Arg Met Asn Leu Gln Thr Leu Arg Gly Tyr
 1               5                  10
```

COMPUTER-AIDED METHOD FOR THE PROVISION, IDENTIFICATION AND DESCRIPTION OF MOLECULES CAPABLE OF EXHIBITING A DESIRED BEHAVIOR, MORE PARTICULARLY IN THE PHARMACEUTICAL SECTOR, AND MOLECULES OBTAINED BY SAID METHOD

CROSS-REFERENCES TO RELATED APPLICATIONS

This application is a continuation-in-part of, and priority is claimed to, International Application No. FR/98/02909 filed December 29, 1998, claiming priority to Application No. 97/16706 filed Dec. 30, 1997 in France.

FIELD OF THE INVENTION

The invention is concerned with computer-aided molecular modelling. In particular, the invention aims to provide a novel computer-aided method which utilises a given number of starting molecules, notably but not exclusively by virtual combinatorial chemistry, for the provision, identification and description of molecules capable of exhibiting a desired behaviour. Such molecules may be used in the agrochemical industry, biomaterials industry, cosmetics industry or the pharmaceutical sector. Preferably, the molecules are used in the pharmaceutical sector.

BACKGROUND OF THE INVENTION

The expression "behaviour" denotes an "activity" in the biological or pharmacological sense, where the molecules relate to pharmaceutical application areas, or a "property" in the physicochemical sense, where the molecules relate to non-pharmaceutical application areas, for example materials such as polymers.

Examples of "behaviours" include anti-bacterial activity, anti-fungal activity, anti-viral activity antibiotic activity, and permeability (e.g. of polymeric membranes for dialysis). Such "behaviours" are discussed elsewhere herein.

In the case of a behaviour for which any given molecule can be represented by a numerical parameter (i.e. a numerical parameter which characterises the degree of activity of that molecule), we may speak of "active molecules" defined as those which have a value of said parameter above a predetermined level, and "inactive molecules" defined as those which have a value of said parameter below that predetermined level.

In fact, e.g. within the class of active molecules, there may be more than one level of activity. For example, we may define classes of "very active", "inactive" and "non-active" molecules. Furthermore, we may choose to classify both agonists and antagonists as being in the active class. Furthermore, the activity may be a toxicity, hence the classes will be "toxic" and "non-toxic", etc.

It is known that research into novel active molecules, notably in the pharmaceutical sector, requires the synthesis of a very large number of molecules which it is then necessary to test in vitro or in vivo. In a best-case scenario only a very small number of these molecules will prove to be active.

In an attempt to rationalise the search for novel active molecules, the idea arose of turning to molecular modelling using computerised data bases.

One technique conventionally employed is Quantitative Structure Activity Relationships (QSAR). This is based on the hypothesis that if a molecule exhibits a given biological behaviour, all the information required to describe that molecule resides in its structure, i.e. in its atoms, bonds and shapes.

In QSAR, a number of known lead compounds which are known to be active are collected. The values of several numerical "descriptors" are derived for each molecule. The lead compounds (and their descriptors) are referred to as a learning set. As discussed below, a descriptor is a numerical parameter characterising the molecule (e.g. dipole moment). QSAR then seeks candidate molecules (i.e. new molecules) for which the descriptor values resemble the descriptor values of the learning set.

Specifically, in conventional "classical" QSAR a linear combination of descriptors is considered. In this linear combination, each descriptor is multiplied by a respective weighting factor, to derive a single numerical parameter f. The values of the weighting factors are set using the active lead compounds, so that the value of f is high for all lead compounds. A candidate molecule is then tested to see whether its value of f is high or low.

A candidate molecule for which the value of f is high (i.e. its descriptor values do resemble the descriptor values of the lead compounds) is predicted to be active, or at least likely to be active. Such a candidate molecule may then be subjected to a (usually more expensive and/or time consuming) test of whether it does indeed exhibit the activity.

Results obtained with the techniques of this type that are known to date have not been satisfactory, in particular owing to inadequate definition of parameters and the inadequacy of linear models.

Furthermore, to obtain a reasonable accuracy in predicting the activity of candidate molecules, it is generally necessary to employ at least one descriptor which can only be measured experimentally. Therefore, in order to predict the activity of a candidate molecule, the candidate molecule must be chemically synthesised.

SUMMARY OF THE INVENTION

It is the object of the present invention to at least partly overcome these drawbacks.

It is a further object of the invention to provide a method of designing a molecule in which only descriptors for which the values may be determined computationally (i.e. without it being necessary to chemically synthesise the compound) are used since computation of a descriptor value is generally relatively cheap, the method permits a large number of candidate molecules to be screened, to determine which molecules are worthy of chemical synthesis and in vitro and in vivo testing.

It is a further object of the invention to permit a non-linear combination of descriptor values.

These objects are achieved in accordance with the invention, which offers a method for the provision, identification and description of molecules exhibiting a desired behaviour, said method being based on computer aided design (CAD) and computer aided screening of virtual combinatorial libraries. This method uses different descriptors—topological, shape, chemical, physical, etc.—in combination with a novel analysis of molecular dynamics trajectories.

In general terms, the present invention proposes that a method of designing molecules employs both "active" and "inactive" lead molecules to derive at least one criterion for predicting whether a candidate molecule (for which the activity is not known) is active or inactive. For a plurality of candidate molecules, the descriptor values are determined, and the activity of the candidate molecules is predicted using the criteria. Candidate molecules which are predicted to be active, may then be tested experimentally to determine whether they are in fact active.

It is found that making use of both active and inactive molecules, and a non-linear combination of their descriptor values, the accuracy of prediction of activity of candidate molecules may be enhanced, for example as compared to classical QSAR described above.

A variety of descriptors may be used, including all kinds of quantitative and/or semi-quantitative properties. For example, as anyone skilled in the art will be aware, from the graphic representation of a molecule, in other words a two-dimensional representation, or 2D representation, of a chemical compound, it is possible to derive a set of numerical values known as "topological descriptors". Moreover, one can use descriptors reflecting certain physicochemical properties such as for example lipophilic character, or lipophilicity, which is expressed as logP, where P is the partition coefficient of the compound in question between water and n-octanol, or molar refractivity. It is furthermore possible to use numerical descriptors representing molecular shapes.

Preferably, all descriptors used are ones which can be determined for a given candidate molecule computationally (i.e. without in vitro or in vivo testing being necessary). The number of descriptors is preferably at least 10, at least 25, at least 50 or at least 100.

Preferably, the criteria include at least one non-linear criterion, that is a criterion which is based on a non-linear function of the descriptor values. Thus, unlike the classical linear QSAR paradigm, in which the biological activity can be expressed as a linear combination of relevant descriptors, the present invention uses a non-linear variable mapping paradigm, in which the activity is a non-linear function of structural, topological and molecular descriptors.

For example, according to one criterion, a molecule may be predicted to be active only if a certain descriptor value is within a range (determined based on the descriptor values of the active and inactive compounds). The range of values of such a filter is preferably derived based on the range of values of the descriptor of the active lead molecules, and the range of descriptor values of the inactive descriptor values. Preferably, the criteria of the method include a plurality of criteria defined on the basis of a respective numerical range.

Thus, such a filter may be defined by the range of variation of a given descriptor for all known active compounds when compared to the range of variation of the same descriptor for all known inactive compounds.

If the "active" range totally covers the "inactive" range, the filter may be of no use, which is the same as saying that the variation in this particular descriptor bears no relation to the biological activity.

If the "active" range does not totally cover the "inactive" range, any molecule that exhibits for this descriptor a value falling within a zone of the "active" range that does not cover the "inactive" range will have a strong probability of also being active.

The predictive capabilities of this kind of approach are improved by the use of several filters (each filter being a descriptor range), typically 10 to 30, each representing a different way to quantify structural and physicochemical properties of a molecule.

If the learning sample corresponds to in vivo tests, the set of filters describes the conditions of activity or inactivity in vivo. In the case of in vitro tests, the set of filters describes the conditions of activity or inactivity in vitro.

The above variety of filter constitutes an objective filter, that is one which is purely numerical. However, the term filter is not limited in this respect, and the filter(s) may include at least one subjective criterion (e.g ease of synthesis, low expected toxicity based on known toxicity properties, etc), by which a human operator assesses subjectively the correlation of descriptor values of candidate molecules to descriptor values of lead molecules. In the case that a subjective (human performed) criterion is employed, the screening is preferably a two-stage process in which firstly objective criteria are used to identify candidate molecule which are predicted to be active, and the subjective criterion is applied subsequently on those identified candidate molecules only.

The method of designing molecules may include testing a plurality of candidate molecules to determine whether they conform to said derived criteria (i.e. have descriptor values within the range(s) associated with activity). That is, each of the criteria constitutes a "filter" for testing candidate molecules.

The filters may include at least one static filter, that is a filter which employs one or more descriptors which characterise a molecule in a static or time averaged state (e.g dipole moment averaged over time).

The filters may further include at least one dynamic filter, that is a filter which employs one of more descriptors which characterize the dynamic behaviour of a molecule. For example, the filter may be an amplitude of flexing of the molecule along one or more axes determined on the basis of the lead compounds.

One example of a dynamic filter is one based on the "conformational space" of a molecule, which is to say the variation in the space occupied by a molecule over a period of time, as determined by molecular modelling techniques. For example, for each molecule of a given set of active and inactive molecules an autocorrelation vector of interatomic distances may be calculated over a predefined period of time, resulting for each molecule in as many autocorrelogram vectors as its conformation undergoes during the said period of time. The set of configurations during the period time is referred to as the conformational space.

One way to represent the autocorrelation vectors is principal component analysis using said conformational spaces as input. The first n principal component vectors are extracted (e.g. where n is an integer), resulting in the distribution of all said conformations of all said molecules on a common plane (if n equals 2). More generally, the area in the n dimensional space which is swept out during the predetermined time is derived.

The conformational spaces of two molecules may be said to have an overlap of x if the overlap of the two respective conformational spaces projected in the n dimensional space of the PCA is x %. Other measures of distance may alternatively be used to compare the proximity of two projected conformational spaces, such as for example a $x^2$ (chi-squared) test, which is a standard statistical method to compare the overlap of two distributions of values.

Thus, for example based on the overlap, an objective dynamic criterion may be established (for example, that the conformational space of a candidate molecule has an overlap with the conformational space of each of the active lead compounds greater than a first predetermined value and/or an overlap with the conformational space of each of the inactive lead compounds of less than a second predetermined value.) Alternatively, the dynamic criterion may be a subjective one, based on a human operator visually assessing the similarity (e.g. overlap) of the conformational spaces of two molecules in the n-dimensional space.

Preferably, the derivation of the criteria is such that the predictive information provided by one criterion is not merely a duplication of predictive information provided by another criterion. In other words, the number of criteria should be selected so that each criterion is as independent as possible of the other criteria. This means that during the screening procedure time, useful predictive information is obtained each time an evaluation is made of whether a candidate molecule satisfies a given criterion (i.e. information which is not redundant from the results of the other criteria).

Thus, the step of deriving criteria preferably includes a step of determining whether two or more derived criteria are correlated in relation to each other, and if so deleting one or more of the correlated criteria.

More specifically, the invention is directed at a computer aided method for the provision, identification and/or description of molecules exhibiting a desired behaviour, notably in the pharmaceutical sector, which method comprises the following steps:

1) producing a learning set of molecules including molecules known to exhibit the activity ("active molecules") and molecules known not to exhibit the activity ("inactive molecules") (the molecules of the learning set may for example be known, closely related molecular structures composed on the one hand of active molecular structures known to exhibit the desired activity and on the other hand of inactive molecular structures known to be devoid of said activity or to exhibit weak desired activity);

2) determining the values of a plurality of descriptors of said learning set of molecules;

3) from said values deriving one or more criteria associating descriptor values with activity, said criteria including both static and dynamic criteria;

4) generating a plurality of candidate molecules, typically closely related molecular structures, more particularly by combinatorial explosion, from the learning set;

5) optionally screening the candidate molecules thus generated, on the basis of the enrichment in molecular diversity terms provided by each molecule in relation to the selected descriptors;

6) subjecting the remaining candidate molecules to at least one said static criteria, and disregarding candidate molecules which do not meet said static criteria;

7) subjecting the remaining candidate molecules to at least one said dynamic criterion (representing the constraints of conformational variation which the molecules must satisfy in order to be active), and disregarding candidate molecules which do not meet said dynamic criteria;

8) synthesising and testing the remaining candidate molecules; and 9) if the anticipated result is not obtained, or if it is only obtained in part, steps 3) to 8) may optionally be repeated, using the inactive synthesised molecules as additional inactive molecules of the learning set.

Within the scope of the invention, the steps need not be performed in order (1)–(8). For example, steps (4) and (3) may be reversed. Thus, the numbering of the steps does not constitute a limitation on the scope of the invention.

The invention is also concerned with a molecule that was not previously known to exhibit a desired behaviour distinguished by the fact that it occupies a conformational space identical or very similar to the conformational space of at least one reference molecule, the reference molecule having been known beforehand to exhibit the desired behaviour. The concept of "very similar" is to be understood in terms of all the conformational spaces corresponding to the molecules tested. For example, the 10% of conformational spaces nearest to the conformational space of the reference molecules are to be considered as "very similar".

An alternative definition of the term "very similar" is that two conformational spaces are "very similar" if the overlap of the conformal spaces is at least 80%, at least 90% or even at least 95%.

Where the method relies on a plurality of reference molecules, the conformational spaces of the reference molecules are to be considered as "very similar".

Generation of the Candidate Molecules

The candidate molecules may be generated, as an additional step of the method, as described in detail below. However, alternatively, it is possible for the candidate molecules to be drawn from a pre-existing library of molecules. Thus, the criteria in this case are used to screen a pre-existing library of compounds to predict their activity.

In the case of generating the molecules during the method itself, this may be done using a "combinatorial explosion". That is, the filter molecules can be used to screen a plurality of virtual compounds generated during a combinatorial explosion, i.e. all the compounds obtained for example by connecting up a list of substituents to predetermined parts of a structural nucleus known as the synthon. The most promising compounds, namely those which satisfy all the constraints defined by the filters, are then synthesised by chemical synthesis or genetic engineering, or else by some other means, and tested in bioassays.

A combinatorial explosion may be generated from the learning set, taking into account the useful conditions of variation for each variable position. For example, if it is noticed that the molecules of the learning set have a structural feature in common, for example the presence of particular groups in particular locations, the candidate molecules can be generated by a combinatorial explosion of molecules which share this feature. To do this it is possible to use substituents data bases defined by their structure and the descriptors derived therefrom.

The combinatorial explosion can be generated using Legion software produced by the Tripos company or another piece of software designed by R. Lahana, the Combex software which creates such an explosion from a "scaffold" or a consensus sequence, and from a list of constraints on each of the substitution points. An SQL (Standard Query Language) type command language makes it possible to combine all kinds of substituent selection conditions at will.

For each combination generated, it is possible to verify the enrichment in terms of molecular diversity provided by the molecule created, relative to the chosen descriptors. If this enrichment is sufficient, the molecule is retained, otherwise it is rejected.

The enrichment in terms of molecular diversity can be verified by means of software designed by R. Lahana, the Diverser software which makes it possible to carry out a quantitative evaluation of the molecular diversity exhibited by any chemical library, even if the molecules comprising it are highly flexible and if said chemical library is purely virtual. This software makes it possible to compare libraries for diversity, to identify "gaps" in diversity within a library, and to rationally design minimal libraries having maximum diversity. The selection techniques may for example be hierarchical classification (clusters) partitions, uniform design, random sampling, etc.

Derivation of the Screening Criteria

Inactive molecules predicted to be active contain unexplored properties that are decisive for the activity. Such properties may be used within the method to derive additional (or refined) criteria for predicting activity. Thus, an iterative improvement of the filters is possible. In this way, after a few repeats, the virtual screening method can be used for the exact identification of compounds exhibiting the properties sought.

In practice, from the starting structures (lead molecules) whose activity can be measured in vitro and/or in vivo, a "learning set" is produced by determining the different physicochemical, structural and molecular parameters that enable active molecules and inactive molecules to be described.

These parameters are represented in the form of ranges of variations, or "constraints", as a function of the activity classes. A filter is defined by a set of constraints.

The quality of the descriptors chosen is controlled in terms of variability, along with the choice of descriptors to be used and the intercorrelation between the descriptors selected.

This can be done using software designed by R. Lahana, the ANODA (ANalysis Of DAta) software which associates with a chemical library a "visiting card" that is straightforward in terms of base descriptors and of analysis into principal components. Various techniques for selecting descriptors are employed, such as analyses of variability, of intercorrelation, and of representativeness (regression, neural networks, genetic algorithms).

"Static" filters, i.e. those which do not depend upon the conformational variability of the molecules, describe the intervals in structural, physicochemical and molecular values to which the molecules must correspond in order to be active. By using these static filters, the molecules that have the maximum chances of being active are derived. These molecules are synthesised if appropriate and tested for the activity sought.

In this step it is possible to use software designed by G. Grassy, the Varimap software which sets up static filters from descriptors obtained by TSAR software, available from the Oxford Molecular Group, Oxford (UK) and the original authors of which are G. Grassy and R. Lahana.

The most promising candidates selected by means of the static filters are then subjected to a dynamic filter, i.e. representative of the conformational variation constraints which the molecules generated must satisfy in order to possibly be active, compared to those of the learning set.

This dynamic filtering can be carried out by means of new software designed by G. Grassy, the Multidyn software, which allows the conformational spaces of any molecules to be characterised on the basis of molecular dynamics trajectories. The bioactive conformations of the molecules in question are accordingly displayed.

The molecule selected on the basis of the filters are then synthesised and tested.

If the biological activity found does not meet, or only partly meets, the expected criteria, the steps of verifying the enrichment in terms of molecular diversity, static filtering, dynamic filtering, synthesis and testing are repeated.

If molecules are found to meet the biological criteria set, then the objective has been achieved.

The method of the invention therefore makes it possible to define novel active molecules by an entirely rational process which at no stage uses hypothesis about their possible mechanism of action or about their possible receptor.

Applications of the Method of the Invention

The method of the invention may be used for the generation of a variety of molecules, including antibacterial, antifungal, antiviral and antiparasitic molecules (as discussed elsewhere herein).

A further aspect of the invention provides molecules obtained or obtainable by the computer aided design methods of the invention. The molecules selected for synthesis may be of various chemical natures, including peptides, peptoids and carbohydrates. In one embodiment the synthesised molecule is of a different chemical nature from the lead molecule, e.g. the lead molecule may be peptidic, but the learning set may comprise peptoids and the synthesised molecule may be a peptoid. Alternatively, the synthesised molecule may be of the same chemical nature as that of the learning set.

The synthesised molecule may be of a smaller size than the molecules of the learning set, for example the molecules of the learning set may be 1500 to 4000 Daltons, or 1000 to 3000 Daltons, or 500 to 2000 Daltons. The synthesised molecules may be shorter by 500 to 1000 Daltons.

In the case of a peptidic learning set the peptides may be 15 to 40, or 10 to 30, or 5 to 20 amino acids long. The synthesised peptides may be shorter than the peptides of the learning set by 5 to 10 amino acids.

Antibacterial molecules include molecules which have have antibacterial activity against a wide range of bacteria. They may have anti-gram negative and/or anti-gram-positive activity. Antibiotic molecules include broad and narrow spectrum antibiotics. Bacteria against which such antibacterial and antibiotic molecules may act include: *Streptococci*, e.g. *Streptococcus pneumoniae*; *Staphylococci*, e.g. *Staphylococcus aureus*; *Salmonella* species, e.g. *S. enteritidis*; *Pseudomonas aeruginosa*; *Escherischia coli*; *S. epidermidis*; and *Corynebacterium xerosis*.

Antifungal molecules include molecules having activity against, *Aspergillus, Candida* and *Mucor* species. The anti fungal activity may be against plant or animal infecting fungi.

Antiparasitic molecules include molecules with activity against nematodes, trypanasomes and Plasmodia.

Antiviral molecules include molecules which have activity against animal or plant viruses. Animal viruses include; HIV-1, HIV-2, HSV-1, HSV-2, HRV, CMV, RSV, HPV, e.g. HPV-16, adenovirus, adeno-associated virus, measles virus or smallpox virus. Plant viruses; TMV, CaMV, PVX and PVY. Antiviral molecules include molecules which interfere with the life cycle of the virus, e.g. with the replication of the virus. They may alternatively inhibit the entry of a virus molecule into a cell, e.g. for animal viruses by blocking the cell surface receptor which allows viral entry. For example, an anti HIV molecule includes molecules which bind to the CD4 receptor on T-cells. For plant viruses, the molecule may block transport of the virus through plasmodesmata, e.g. by inhibiting the viral movement protein.

Following identification of a molecule in accordance with the method of the present invention, the substance may be investigated further. Furthermore, it may be manufactured and/or used in preparation, i.e. manufacture or formulation, of a composition such as a medicament, pharmaceutical composition or drug. It may itself be used in the generation of mimetic molecules according to the method disclosed herein or any other suitable technique known to those skilled in the art.

The designing of molecules according to the method of the invention might be desirable where it is difficult or expensive to synthesise known molecules having the desired behaviour or where it is unsuitable for a particular method of administration, e.g. peptides are not well suited as active agents for oral compositions as they tend to be quickly degraded by proteases in the alimentary canal. The methods disclosed herein may be used to avoid randomly screening large number of molecules for a target property.

The molecule or composition may be used in a variety of contexts depending upon the criteria set (e.g. biological activity, physiochemical properties) in the method of the invention. By way of example the molecules may be used:
(i) as pharmaceuticals, e.g. anti-bacterial molecules, anti-fungal molecules, anti-viral, anti-parasitic molecules, antibiotics, immuno-stimulatory molecules, e.g. for use in vaccines or immuno-suppressants;
(ii) as cosmetics e.g. new molecules with a deodorant effect. Undesirable body odours are caused by bacteria, typically gram positive aerobic bacteria e.g. *Corynebacterium xerosis* or negative coagulase anaerobic micrococci e.g. *S. epidermidis*. Using the method of the present invention it is possible to design new antibacterial molecules (e.g. peptide-based) whose antibacterial effect is targetted specifically to the odour-causing bacteria;
(iii) in veterinary applications. New molecules may be designed to protect bodily fluids (e.g. semen) from microbial infection during storage. For example, pig semen is typically stored at a relatively high-temperature (approximately 20° C.). At such temperatures bacteria proliferate. Some of the bacterial strains are resistant to known antibiotics. Using the method of the present invention antibiotic molecules may be designed which have broad spectrum anti-bacterial activity (including anti-gram negative and anti-gram positive activities) whilst not exhibiting significant spermicidal activity;
(iv) as agrochemicals, e.g. mimics of natural peptides having antifungal, antibacterial or antiviral activity may be designed. Such peptides are preferably non-toxic to humans and may be expressed directly in genetically modified plants;
(v) as biomaterials, molecules may be designed which favour certain dialysis membrane properties. Starting from a known polymeric membrane which is used for dialysis purposes (e.g. human dialysis), new molecules may be designed with improved permeability or dialysis properties, such molecules can be used as additives to the polymeric membrane.

Thus, the present invention extends in various further aspects to a molecule identified or defined in accordance with a method of the present invention, and also a pharmaceutical composition, medicament, drug or other composition comprising such a molecule, a method comprising administration of such a composition to a patient, e.g. for antibacterial/antibiotic/anti-fungal/antiviral treatment, which may include preventative treatment, use of such a substance in manufacture of a composition for administration, e.g. for antibacterial antibiotic/antifungal/antiviral treatment, and a method of making a pharmaceutical composition comprising admixing such a substance with a pharmaceutically acceptable excipient, vehicle or carrier, and optionally other ingredients.

The invention further provides preservative compositions, e.g for preserving bodily fluids, or cosmetic preparations e.g. deodorants.

A substance obtained or obtainable using a method of the present invention may be peptide or non-peptide in nature. Non-peptide "small molecules" are often preferred for many in vivo pharmaceutical uses.

Peptoids are one example of non-peptidic mimics. Unlike peptides, in peptoid molecules the side chain groups are bonded to nitrogen rather than to carbon. Peptoids may be synthesised by the polymerisation of N-substituted glycine residues. The N-substitutions can be any suitable side chain found in amino acids, so N-Ala would be glycine which is N substituted with $CH_3$ (See Simon, R J et al., 1992, Peptoids: A Modular Approach to Drug Discovery, *Proc. Natl. Acad. Sci. USA*, 89:9367–71; which is incorporated herein by reference).

A peptoid backbone is shown below:

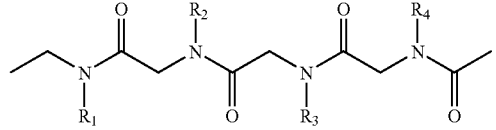

In addition to peptoids, other mimic molecules include pseudopeptides, retro-inverso peptides, and peptide bond mimics as described in the following articles, which are incorporated herein by reference: Emmons et al., Current Opinion in Biotechnology, 1997, 8: 435–441; Olson et al., Journal of Medicinal Chemistry, 1993, 8 (21):3039–3049; Fletcher and Campbell, Chem. Rev., 1998, 98: 763–795; Marraud et al., Biopolymers, 1993, 33: 1135–1148; Gante, Angew. Chem. Int. Ed. Engl., 1994, 33: 1699–1720.

A convenient way of producing a polypeptide is to express nucleic acid encoding it. This may conveniently be achieved by growing in culture a host cell containing the nucleic acid under appropriate conditions which cause or allow expression of the polypeptide. The nucleic acid may be introduced alone or as part of a vector, and may be extragenomic or integrated into the genome. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

The introduction of DNA may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Following production by expression, a polypeptide may be isolated and/or purified from the host cell and/or culture medium, as the case may be.

Peptides can also be generated wholly or partly by chemical synthesis. The well-established, standard liquid or solid-phase peptide synthesis methods can be used, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A molecule defined by a method of the present invention, or a composition containing such a molecule may be provided in a kit, e.g. sealed in a suitable container which protects its contents from the external environment. Such a kit may include instructions for use.

EXAMPLE

The method of the invention was successfully employed in the pharmacomodulation of molecules in order to enhance the performance of these in vitro and especially in vivo.

The detailed example of implementation which follows serves to illustrate and better explain the invention.

Obtaining Novel Immunomodulatory Compounds

It has recently been shown that peptide 2702.75-84 (a peptide derived from HLA-B2702, amino acids 75 to 84) prolongs heart-allograft survival in mice (Transplantation, vol. 59, page 455 (1995).

Administration of peptide 2702.75-84 in a dose of 80 mg/kg/day for 10 days following transplantation of B6 donor hearts into CBA recipients prolongs heart-allograft survival to 11.4 2.6 (n=8) days, compared to 8.2 1.2 days in untreated control animals (p<0.01). No effect on graft survival was observed following treatment with peptide 2072.75-84 at lower doses.

The in vivo activity of several peptides (n=19) derived from peptide 2702.75-84 and from other MHC/HLA sequences was similarly evaluated. The peptides tested comprised peptides of amino acid types D and L. Certain peptides differed from peptide 2702.75-84 at up to six amino acid positions, others had an inverted sequence.

All of these peptides, the sequences of which are represented in Table 1 below, were synthesised using F-moc/tBu chemistry and then tested.

Studies into the response to doses by mice having received a heart-allograft were carried out using peptides in acetate form, purified to more than 90 by high performance liquid chromatography (HPLC).

Abdominal heterotopic heart transplantation was carried out as described previously in J. Thorac. Cardiovasc. Surg., vol. 7, page 225 (1969).

CBA mouse recipients of C57B1/6 donor hearts were treated daily with different doses of peptide following organ transplantation. Peptides were dissolved in DMSO and diluted in PBS (final DMSO concentration 10%) before intraperitoneal administration. Animals were treated from the day of transplantation until day nine. Graft survival was monitored daily by direct palpation, and rejection was defined as termination of palpable cardiac contractility. The statistical significance of prolongation of heart allograft survival was calculated using the Mann-Whitney test.

Treating the mouse heart allo-graft recipients with certain of these peptides (n=9; in bold type in Table 1 below) made it possible to significantly prolong graft survival, whereas the others had no significant effects.

The structures of the peptides utilised and the results obtain ed are presented in following Table 1.

TABLE 1

| Peptide sequence | HLA/MHC | MSTSD |
|---|---|---|
| untreated | | 7.5 1.1 |
| RENLRIALRY | B2702 | 11.4 2.6 (1)* |
| YRLAIRLNER | — | 12.1 2.8 (2) |
| renlrialry | — | 11.4 4.1 (1) |
| yrlairlner | — | 13.2 2.7 (2) |
| RVNLRIALRY | — | 11.5 0.5 (3) |
| YRLAIRLNVR | — | 12.5 1.6 (4) |
| rvnlrialry | — | 13.1 3.9 (3) |
| yrlairlnvr | — | 12.2 2.9 (4) |
| NLRIALRYYW | — | 11.6 1.3 (5) |
| RVNLRTALRY | Kk | 8.5 0.7 (6) |
| RVDLRTLLRY | Dk | 7.0 0.5 (7) |
| RVDKRTLLGY | Kb | 7.8 1.0 (8) |
| RVSLRNLLGY | Db | 8.0 0.5 (9) |
| RESLRLLRGY | 07 | 7.5 0.7 (10) |
| REDLRTLLRY | B2705 | 7.7 1.2 (11) |
| ENLRIALR | — | 8.5 0.7 (12) |
| renlpialry | — | 9.5 2.4 (13) |
| RVNLRTLRRY | E | 8.0 0.5 (14) |
| RMNLQTLRGY | G | 7.5 0.7 (15) |

These 27 descriptors included the dipole moment, which was calculated based on a fully extended conformation of each peptide. Statistical analysis showed that 14 descriptors correlated with each other. Consequently they were not used for the definition of constraints that differentiated between active and inactive peptides. The 13 other conformation-independent descriptors were used to build a static filter for screening a virtual combinatorial library as described further below.

TABLE II

The 27 topological and physicochemical descriptors used

| Property | Nature | Included/excluded |
| --- | --- | --- |
| Molar mass | Physical | Excluded |
| Ellipsoidal volume | Shape | Included |
| Molecular volume | Shape | Included |
| Molar refractivity | Topological | Included |
| Lipophilicity (LogP) | Topological | Included |
| Kappa 1 | Topological | Excluded |
| Kappa 2 | Topological | Excluded |
| Kappa 3 | Topological | Excluded |
| Kappa alpha 1 | Topological | Excluded |
| Kappa alpha 2 | Topological | Included |
| Kappa alpha 3 | Topological | Excluded |
| Flexibility | Topological | Included |
| Kier Chi V4 | Topological | Included |
| Randic index | Topological | Excluded |
| Balaban index | Topological | Included |
| Wiener index | Topological | Excluded |
| E-state sum | Physical | Excluded |
| Dipole moment | Physical | Included |
| Number of C atoms | Chemical | Excluded |
| Number of O atoms | Chemical | Included |
| Number of N atoms | Chemical | Included |
| Number of H atoms | Chemical | Excluded |
| Total number of atoms | Chemical | Excluded |
| Number of methyl groups | Chemical | Excluded |
| Number of ethyl groups | Chemical | Included |
| Number of amino groups | Chemical | Excluded |
| Number of hydroxyl groups | Chemical | Included |

The topological descriptors listed above were used to calculate static filters. Thirteen descriptors (shown in normal vertical type) supplied information about the characteristics of peptides having immunomodulatory activity and were used to define constraints for screening a virtual combinatorial library. The fourteen other descriptors proved to be correlated with each other and were excluded from the analysis.

Using the Combex program (Synt:em, Nimes, France), a combinatorial explosion was generated based on a consensus sequence RXXXRXXXXY (SEQ ID NO: 16), derived from the learning set after aligning all active and inactive sequences. This sequence left seven positions, the positions represented by "X", to mutate in order to create the library.

All molecules were generated using the SMILES convention, and then converted into a 3D structure using Corina software (Oxford Molecular Group, Oxford, UK).

Initially, both natural and unnatural amino acids were included in the substituents data base. All amino acids were described in terms of physicochemical properties (lipophilicity, basicity, aromaticity, etc.) and also by topological descriptors (Kier analysis, Balaban index, etc.). The use of 35 amino acids led to 35$^7$ combinations (64 billion compounds), which was still in excess of the capacity of the computer used.

In order to decrease this number, certain supplementary data such as the lipophilicity distribution were taken into account. The structure of the lead compound (2702.75-84) exhibited two lipophilic domains separated by hydrophilic residues. This suggested that such a distribution was important for activity. In order to take this distribution into account, the Applicant decided to use the following list of amino acids for each of the 7 positions: V, I, T, W, L, nL (NL=Nor-Leucin). Thus, the number of compounds in the library was reduced to 6$^7$ combinations (279,936 compounds).

To screen the virtual combinatorial library, the corresponding set of properties was calculated "on the fly" in respect of each structure generated by the Combex software. These properties were analysed using the predefined static and dynamic filters, based on the constraints, and only those compounds that satisfied all the constraints were retained.

The static filters, obtained by the ranges of variation of the retained descriptors, were based on the set of conformation-independent constraints which was defined using the learning set of active and inactive compounds. They were designed using the Varimap software (Synt:em, Nimes, France).

Screening the library of 279,936 compounds with these static filters resulted in the identification of 26 peptides that satisfied all constraints. Among these the peptides were investigated from the aspect of their conformational spaces (dynamic filter), and five in particular were investigated, designated respectively as RDP1257, RDP1258, RDP1259, RDP1271 and RDP1277.

The flexible nature of the peptides was analysed using molecular dynamics (MD) simulations.

The MD simulations of peptides solvated with periodic conditions were performed using AMBER 4.1 software (Oxford Molecular Group, Oxford, UK). It used 1015 ps in duration for each solvated peptide. The dielectric constant was set to the unit. The temperature of the system was initially increased gradually from 10 to 300 K, during a time period of 15 ps. During simulation a constant temperature was maintained at 300±10 K by coupling to an external bath with a relaxation time of 0.1 ps. The time step chosen was 1 fs. The computational time was approximately 0.5 h per ps. A 10 angstroms residue-based cutoff was used for all non-bonded interactions. The non-bonded pair list was updated every 10 fs and the coordinates were collected every 1 ps during the trajectories, which resulted in a set of 1015 conformations for each trajectory. In all trajectories, no constraints were applied to the atoms and no cross terms were used in the energy expression.

Each conformation was represented by a shape descriptor called the 3D autocorrelation vector (hereinafter 3D-ACV) [Eur. J. Med. Chem.-Chim. Theor., vol. 19, page 61 (1984)]. A set of 3D-ACVs was calculated for each series of conformations obtained by molecular dynamics (MD), and then processed using multivariate statistics (Trends in QSAR and Molecular modelling 92 ESCOM Publishers, page 216 (1993)]. This was done in three main steps (i to iii):

(i) For a given conformation of the studied molecule, in this case a peptide, the corresponding 3D-ACV descriptor was calculated as follows. The distances between all pairs of atoms were calculated. The distribution of these distances was a vector of which each bin was the sum of atom pairs in a specific range of interatomic separation, i.e. where two given atoms were separated by between (r–1) and r angstroms. In this study the step was equal to 1 angstrom. Obviously, the slightest modification in the conformation of said molecule results in a change in the distribution of the interatomic distances, and hence in a modification of the 3D-ACV. Consequently, this descriptor is one of the most effective in representing the conformational shapes of molecules.

(ii) An MD trajectory is the set of conformations adopted by a given molecule during the MD simulation. For each conformation, the corresponding 3D-ACV was calculated "on the fly" and stored. This multiple 3D-ACV, a function of time, is a descriptor of the dynamic behaviour of said molecule.

(iii) For the comparison of the multiple 3D-ACVs representing the trajectories of the set of molecules analysed, principal component analysis (PCA) was applied to each of these multiple 3D-ACVs. This transformation reduced the dimensions of the data set to a smaller number (a 2D space in the present case) and also made it possible to project all the trajectories of all the molecules on one plane. In this reduced space, each molecule is represented by a set of dots, i.e. its conformations throughout the entire MD simulation, which represents its conformational space. The molecules could then be compared with one another in terms of conformational spaces. Analyses of trajectories and conformational spaces were calculated by means of Multidyn software (Synt:em, Nîmes, France).

The use of a dynamic filter to screen the peptides in terms of conformational spaces revealed that 4 of these 5 peptides occupied the same conformational space or a very similar space but that one, RDP1277, was different in this regard.

These 5 peptides were synthesised and tested in heart-allograft survival bioassays.

At a dose of 10 mg/kg/day, all the peptides except for RDP1277 were active in vivo. No significant prolongation of graft survival was observed after therapy with RDP1277 (MST=9.0 1.4). Conversely, therapy with all the other peptides resulted in significant prolongation of graft survival, ranging from 11 to 13 days.

Supplementary tests with the peptide RDP1258 at doses of 1 to 10 mg/kg/day revealed enhanced efficacy of the therapy at the lower doses. At a dose of 1 mg/kg/day, 30% of the mice that received a heart allograft and were treated with RDP1258 survived for more than 100 days, while the reference peptide, 2705.75-84, prolonged allograft survival after treatment at a dose of 80 mg/kg/day, whereas no effect was observed at lower doses. Moreover, no long-term graft survival was induced by administering this reference peptide.

The strategy according to the invention therefore made it possible to rationally design several bioactive compounds which proved to have a greater activity than that of the active molecules of the learning set.

The example of the method of the invention explained above was performed using one Silicon Graphics *Indigo* w2 workstation with a 180 MHz R5000 processor, 128 Mbyte memory, 2 Gbyte system disc and a 19 inch monitor with a cluster of 16 Hewlett Packard 730 workstations with 64 Mbyte memory each and a total disk space of 32 Gbytes.

Presently, the inventors are using an operating system made up of Unix. 7 Silicon Graphics $O_2$ workstations, each with a 195 MHz R5000 processor, 128 Mbyte memory, 2 Gbyte System disc, and a 19 inch monitor; and 3 Silicon Graphics Origin 200 servers, each having 4×225 MHz R10000 processors with 2 MByte cache memory, 512 Mbyte memory, 18 Gbyte disc space, 1 Craylink, 1DLT tape streamer. The operating system was Irix 6.3. The above units are all networked using a TCP/IP protocol and the disc space is shared using NFS/NIS protocol.

What is claimed is:

1. A computer-aided method for the provision, and identification of molecules exhibiting a desired activity comprising:
- a molecular modeling step in which molecular descriptors are selected computationally;
- a step of building a combinatorial library of molecules;
- a step of selecting candidate molecules from the combinatorial library which potentially exhibit said desired activity;
- a filtering step whereby the candidate molecules are filtered using at least one static filter representing a plurality of said molecular descriptors which each candidate molecule must satisfy in order to exhibit said desired activity; and
- a further filtering step whereby the filtered candidate molecules are further filtered using at least one dynamic filter representing constraints of conformational variations which each candidate molecule must satisfy in order to exhibit said desired activity;
- wherein the filtering steps allow for the identification of molecules exhibiting said desired activity.

2. A computer-aided method according to claim 1 wherein said dynamic filter is based on a shape descriptor derived from a 3-D autocorrelation vector (3D-ACV).

3. A computer-aided method according to claim 2 wherein the static filter is based on physiochemical and topological descriptors at least some of which are chosen from the following descriptors: molar mass; ellipsiodal volume; molecular volume; molar refractivity; lipophilia (LogP); kappa 1; kappa 2; kappa 3; kappa alpha 1; kappa alpha 2; kappa alpha 3; flexibility; kier chi v4; randic index; balaban index; weiner index; sum of condition E; dipolar moment; number of C atoms; number of O atoms; number of N atoms; number of H atoms; total number of atoms; number of methyl groups; number of ethyl groups; number of amino groups; and number of hydroxyl groups.

4. A computer-aided method according to claim 1 wherein the combinatorial library building step comprises building a combinatorial peptide library.

5. A computer-aided method according to claim 1 wherein the combinatorial library building step comprises building a combinatorial peptoid library.

6. A computer-aided method according to claim 1 wherein the static filter is based on physiochemical and topological descriptors at least some of which are chosen from the following descriptors: molar mass; ellipsiodal volume; molecular volume; molar refractivity; lipophilia (LogP); kappa 1; kappa 2; kappa 3; kappa alpha 1; kappa alpha 2; kappa alpha 3; flexibility; kier chi v4; randic index; balaban index; weiner index; sum of condition E; bipolar moment; number of C atoms; number of O atoms; number of n atoms; number of H atoms; total number of atoms; number of methyl groups; number of ethyl groups; number of amino groups; and number of hydroxyl groups.

7. A computer-aided method for the provision and identification of molecules exhibiting immunomodulatory activity comprising:
- a step of molecular modeling in which molecular descriptors of a molecule having immunomodulatory activity are selected computationally;
- a step of building a combinatorial library including molecules having said immunomodulatory activity;
- a step of selecting candidate molecules from the combinatorial library which are potentially immunomodulatory;
- a filtering step whereby the candidate molecules are filtered using at least one static filter representing a plurality of said molecular descriptors which each candidate molecule must satisfy in order to exhibit said immunomodulatory activity; and
- a further filtering step whereby the filtered candidate molecules are further filtered using at least one dynamic filter representing constraints of conformational variations which each candidate molecule must satisfy in order to exhibit said immunomodulatory activity;
- wherein the filtering steps allow for the identification of molecules exhibiting said immunomodulatory activity.

* * * * *